United States Patent [19]

Friebe et al.

[11] Patent Number: 5,399,575
[45] Date of Patent: Mar. 21, 1995

[54] PYRIDINE COMPOUNDS WHICH HAVE USEFUL PHARMACEUTICAL ACTIVITY

[75] Inventors: Walter-Gunar Friebe, Mannheim; Wolfgang Kampe, Heddesheim; Marcel Linssen, Bobenheim-Roxheim; Otto-Henning Wilhelms, Weinheim-Rittenweier, all of Germany

[73] Assignee: Boehringer Mannheim GmbH, Mannheim, Germany

[21] Appl. No.: 66,058

[22] PCT Filed: Nov. 28, 1991

[86] PCT No.: PCT/EP91/02249

§ 371 Date: Jun. 14, 1993

§ 102(e) Date: Jun. 14, 1993

[87] PCT Pub. No.: WO92/09598

PCT Pub. Date: Jun. 11, 1992

[30] Foreign Application Priority Data

Dec. 1, 1990 [DE] Germany ............ 40 38 335.0

[51] Int. Cl.⁶ .................. C07D 213/54; A61K 31/44
[52] U.S. Cl. ................. 514/340; 514/344; 514/357; 546/276; 546/286; 546/330; 546/333; 546/334; 546/335; 546/336
[58] Field of Search ........... 546/286, 330, 333, 276, 546/334, 335, 336; 514/340, 344, 357

[56] References Cited

U.S. PATENT DOCUMENTS

| | | |
|---|---|---|
| 4,271,170 | 6/1981 | Tanouchi et al. ............ 546/286 |
| 4,317,828 | 3/1982 | Tanouchi et al. ............ 546/286 |
| 4,427,682 | 1/1984 | Tanouchi et al. ............ 546/286 |

OTHER PUBLICATIONS

Honma et al, *J. of Med. Chem*, vol. 27, pp. 125–128, 1934.

*Primary Examiner*—C. Warren Ivy
*Assistant Examiner*—Zinna N. Davis
*Attorney, Agent, or Firm*—Nikaido, Marmelstein, Murray & Oram

[57] ABSTRACT

Compounds of the formula I

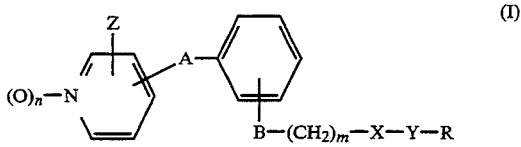

in which A signifies an alkylene radical with 1 to 3 carbon atoms or a group —CH=CH—, B an oxygen atom or a valency bond, m a whole number from 0 to 5, n the number 0 or 1, X a valency bond, an oxygen atom or a sulphur atom, Y a valency bond or a phenylene radical substituted, if desired, one or more times by $C_1$- to $C_6$-alkyl, $C_1$- to $C_6$-alkoxy, halogen, hydroxyl or aminocarbonyl, Z hydrogen, halogen, $C_1$- to $C_6$-alkyl or cyano and R a group CN, COOH, COO$C_1$- to $C_6$-alkyl, CONH-tetrazolyl, CON(OH)($C_1$-$C_6$-alkyl) or 5-(1H)-tetrazolyl, as well as, for the case that Y represents a phenylene radical, also hydrogen, with the exception of the compound 4-[2-(4)-pyridinovinyl]-carboxymethoxybenzene, their physiologically compatible salts and processes for their preparation, as well as medicaments containing these compounds for the treatment of allergic diseases.

6 Claims, No Drawings

PYRIDINE COMPOUNDS WHICH HAVE USEFUL PHARMACEUTICAL ACTIVITY

The present invention concerns new pyridine derivatives of the general formula I

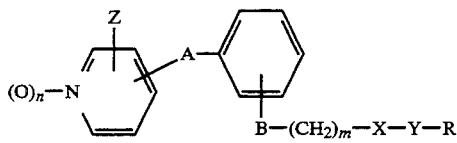
(I)

in which A signifies an alkylene radical with 1 to 3 carbon atoms or a group —CH=CH—, B an oxygen atom or a valency bond, m a whole number from 0 to 5, n the number 0 or 1, X a valency bond, an oxygen atom or a sulphur atom, Y a valency bond, a phenylene radical substituted, if desired, one or more times by $C_1$- to $C_6$-alkyl, $C_1$- to $C_6$-alkoxy, halogen, hydroxyl or aminocarbonyl, Z hydrogen, halogen or $C_1$- to $C_6$-alkyl or cyano and R a group CN, COOH, COO$C_1$- to $C_6$-alkyl, CONH-tetrazolyl, —CON(OH)($C_1$-$C_6$-alkyl) or 5-(1H)-tetrazolyl, as well as for the case that Y represents a phenylene radical also hydrogen, with the exception of the compound 4-[2-(4)-pyridinovinyl]-carboxymethoxybenzene, their physiologically compatible salts and processes for their preparation, as well as medicaments containing these compounds.

Compounds of the formula I, in which A=an alkylene chain, B=an oxygen atom or a valency, m=a whole number from 0 to 5, n=0, X=valency and Y=-valency, Z=hydrogen or alkyl, R=CN, COOH and COOalk are, in part, described in DE-A-2 951 786 as thromboxane synthebase inhibitors. In DE-A-3 641 024 the compound 4-[2-(4)-pyridinovinyl]-carboxymethoxybenzene is mentioned by name which finds use as liquid crystal component.

The new compounds of the general formula I display valuable pharmacological properties, in particular they can inhibit the antigen-caused contraction of lung tissue strips. Therefore, they are suitable for the treatment of allergic diseases, as well as of inflammation-caused bronchospastic and bronchoconstrictory reactions.

The alkyl radical in the mentioned groups can be straight-chained or branched. Preferred alkyl radicals are the methyl, ethyl, n-propyl, isopropyl, n-butyl, isobutyl, tert.-butyl, n-pentyl and 3-pentyl radical.

Halogen atoms are especially flourine, chlorine and bromine.

The bonding of the radical A can take place in 2-, 3- or 4-position of the pyridine, of the radical B in 2-, 3- or 4-position of the phenyl ring.

Especially preferred are compounds of the formula I in which A, B, m, n, X, Y and Z have the given meaning and R signifies a group CO-NH-tetrazolyl, —CON-(OH)($C_1$-$C_6$-alkyl) or 5-(1H)-tetrazolyl.

Furthermore, compounds of the formula I are preferred in which A, B, m, n, Y, Z and R have the given meaning and Y represents a phenylene radical substituted if desired.

Apart from the compounds mentioned in the Examples, the subject of the present invention are, in particular, all substances which display every possible combination of the substituents mentioned in the examples.

The process according to the invention for the preparation of the compounds of formula I is characterised in that, in per se known manner, one either a) reacts a compound of the general formula II

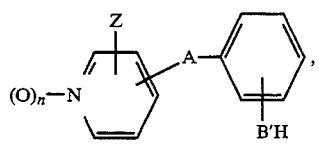
(II)

in which A, Z and n have the given meaning and B' signifies an oxygen atom, with a compound of the general formula III

(III), in which X, Y, R and m have the given meaning and G represents a reactive radical, or b) reacts a compound of the general formula IV

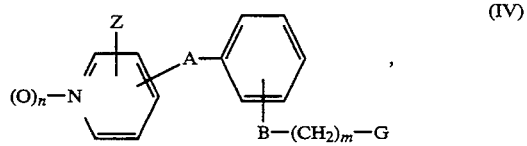
(IV)

in which A, B, G, Z, m and n have the given meaning, with a compound of the general formula V

(V), in which R, X and Y have the given meaning, or c) for the case that A signifies the group —CH=CH—, reacts a compound of the general formula VI

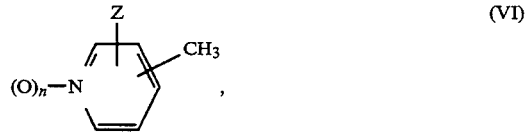
(VI)

in which Z and n have the given meaning, with a compound of the general formula VII

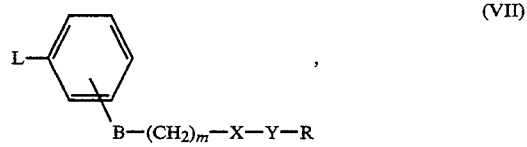
(VII)

in which B, X, Y, R and m have the given meaning and L represents a formyl group or a reactive derivative hereof, and subsequently, if desired, converts a substituent R into another substituent R given by the definition or a group A into another group A given by the definition or oxidises the pyridine nitrogen and, if desired, converts the compound obtained of the formula I into a salt by reaction with physiologically compatible acids or bases.

As reactive residues G, there come into question chlorine, bromine, mesyloxy or tosyloxy. A conversion of the radical R into another radical R defined by the claim takes place, for example, by reaction of a compound of the formula I, in which R stands for a cyano group, with hydrazoic acid or a metal azide and a proton-providing substance, such as for example ammonium chloride, to the tetrazolyl radical or with aqueous acids or lyes to the carboxyl radical. A carboxyl group standing for R can, if desired, be esterified or amidated via a reactive derivative, such as an acid halide, acid anhydride or imidazolide; From an alkoxycarbonyl group standing for R there can be obtained the carboxylic acid by acidic or basic hydrolysis, a carboxamide by aminolysis.

The reaction of compounds of the formulae II and II or IV and V, respectively, expediently takes place in neutral or basic medium, for example in water or a lower alcohol, such as methanol, ethanol or isopropanol, in the presence of an alkali metal alcoholate or alkali metal hydroxide or in aprotic solvents, such as acetone, butanone or dimethylformamide, in the presence of an acid-binding agent, such as sodium carbonate, potassium carbonate or calcium carbonate, at temperatures between 0° C. and the boiling point of the reaction mixture.

One carries out the reaction of compounds of the formulae VI and VII without solvent at elevated temperature, if desired under pressure, or in the presence of a water-binding agent, such as concentrated hydrochloride acid or acetic acid anhydride, with warming.

The starting compounds II to VII are substances known from the literature or can be prepared in analogy to processes known from the literature.

As pharmacologically compatible salts, there come into question especially alkali metal, alkaline earth metal and ammonium salts, as well as possibly salts with non-toxic inorganic or organic acids, such as e.g. hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

One obtains the salts in the usual way, e.g. by neutralisation of the compounds of the formula I with the appropriate lyes or acids.

For the preparation of medicaments, the compounds of the general formula I are mixed in per se known manner with suitable pharmaceutical carrier substances, aroma, flavouring and colouring materials and formed, for example, as tablets or coated tablets or, with addition of appropriate adjuvants, suspended or dissolved in water or oil, such as e.g. olive oil.

The substances of the general formula I can be administered orally and parenterally in liquid or solid form. As injection medium, water is preferably used which contains the stabilising agents, solubilising agent and/or buffers usual in the case of injection solutions. Such additives are e.g. tartrate or borate buffers, ethanol, dimethyl sulphoxide, complex formers (such as ethylenediaminetetraacetic acid), high molecular polymers (such as liquid polyethylene oxide) for viscosity regulation or polyethylene derivatives of sorbitol anhydrides.

Solid carrier materials are e.g. starch, lactose, mannitol, methyl cellulose, talc, highly dispersed silicic acid, high molecular polymers (such as polyethylene glycols).

Compositions suitable for oral administration can, if desired, contain flavouring and sweetening materials. For external use, the substances I according to the invention can also be used in the form of powders and salves. For this purpose, they can be mixed e.g. with powdered, physiologically-compatible dilution agents or usual salve bases, respectively.

The administered dose depends upon the age, the state of health and the weight of the recipient, the extent of the disease, the nature of further treatments possibly carried out simultaneously, the frequency of the treatments and the nature of the desired action. Usually, the daily dose of the active compound amounts to 0.1 to 50 mg/kg body weight. Normally, 0.5 to 40 and preferably 1.0 to 20 mg/kg/day in one or more administrations per day are effective in order to obtain the desired results.

Apart from the substances mentioned in the Examples, in the meaning of the present invention the following compounds are preferred:

4-{4-[2-(2-pyridinyl)-ethenyl]-phenylmethoxy}-benzonitrile

4-{2-[2-(2-pyridinyl)-ethenyl]-phenylmethoxy}-benzonitrile

4-{4-[2-(4-pyridinyl)-ethyl]-phenylmethoxy}-benzonitrile

4-[2-(4-phenoxymethylphenyl)-ethyl]-pyridine 4-{2-[4-(4-chlorophenoxymethyl)-phenyl]-ethenyl}-pyridine 4-{2-[4-(4-methoxyphenoxymethyl)-phenyl]-ethenyl}-pyridine 4-{2-[4-(4-methylphenoxymethyl)-phenyl]-ethenyl}-pyridine 4-{2-[4-(3,4-dichlorophenoxymethyl)-phenyl]-ethenyl}-pyridine 4-{2-[4-(4-hydroxyphenoxymethyl)-phenyl]-ethenyl}-pyridine 5-{4-{4-[2-(4-pyridinyl)-ethenyl]-phenylmethoxy}-phenyl}-1H-tetrazole 4-{4-[2-(4-pyridinyl)-ethenyl]-phenylmethoxy}-benzamide 4-{4-[2-(4-pyridinyl)-ethenyl]-phenylmethoxy}-benzoic acid N-(1H-tetrazol-5-yl)-amide 4-{4-[2-(4-N-oxidopyridinyl)-ethyl]-phenoxy}-butyric acid N-(1H-tetrazol-5-yl)-amide

EXAMPLE 1

5-{4-[2-(4-Pyridinyl)-ethenyl]-phenoxy}-valeronitrile

To the solution of 1.16 g (50 mmol) sodium in 250 ml 2-propanol one adds 10.0 g (50 mmol) 4-[2-(4-pyridinyl)-ethenyl]-phenol, heats under reflux for 10 min, allows to cool, adds thereto 8.1 g (50 mmol) 5-bromovaleronitrile and heats to reflux for 16 h. One evaporates, mixes with water, extracts with dichloromethane, dries the extract, evaporates and triturates the residue with ether. One obtains 11.9 g of title compound (86% of theory) of the m.p. 85°–87° C.

EXAMPLE 2

In a manner analogous to that described in Example 1, one obtains:

| designation | yield % | melting point °C. (solvent) |
|---|---|---|
| a) 4-{4-[2-(4-pyridinyl-ethenyl]-phenoxymethyl}-benzonitrile from 4-[2-(4-pyridinyl)-ethenylphenol and 4-bromomethylbenzonitrile | 72 | 134–135 (ether) |
| b) 5-{4-[2-(2-pyridinyl)-ethenyl]-phenoxy}-valeronitrile from 4-[2-(2-pyridinyl)-ethenyl]-phenol and 5-bromovaleronitrile | 92 | 76–80 (ether) |
| c) 5-{2-[2-(4-pyridinyl)- | 74 | oil |

| designation | yield % | melting point °C. (solvent) |
|---|---|---|
| ethenyl]-phenoxy}-valeronitrile from 2-[2-(4-pyridinyl)-ethenyl]-phenol and 5-bromovaleronitrile | | |
| d) 5-{3-[2-(4-pyridinyl)-ethenyl]-phenoxy}-valeronitrile from 3-[2-(4-pyridinyl)-ethenyl]-phenol and 5-bromovaleronitrile | 44 | 75–76 (ether) |
| e) 5-{3-[2-(2-pyridinyl)-ethyl]-phenoxy}-valeronitrile from 3-[2-(2-pyridinyl)-ethyl]-phenol and 5-bromo-valeronitrile | 23 | oil |
| f) 2-{4-{4-[2-(4-pyridinyl)-ethenyl]-phenoxy}-butylthio}-benzoic acid methyl ester from 4-[2-(4-pyridinyl)-ethenyl]-phenol and 2-(4-bromobutylthio)-benzoic acid methyl ester | 85 | oil |
| g) 2-{4-{4-[2-(4-pyridinyl)-ethyl]-phenoxy}-butylthio}-benzoic acid methyl ester from 4[2-(4-pyridinyl)-ethenyl]-phenol and 2-(4-bromo-butylthio)-benzoic acid methyl ester | 70 | oil |

EXAMPLE 3

4-[2-(2-Pyridinyl)-ethenyl]-benzonitrile

A mixture of 20.4 g (0.2 mol) acetic acid anhydride, 18.6 g (0.2 mol) 2-methylpyridine and 26.2 g (0.2 mol) 4-cyanobenzaldehyde is heated to reflux for 24 h. One allows to cool, mixes with excess ether and filters. One isolates 18.8 g of title compound (46% of theory) of the m.p. 98°–98° C.

EXAMPLE 4

4-{4-[2-(4-Pyridinyl)-ethenyl]-phenoxy}-butyric acid ethyl ester

One heats a mixture of 30 g (0.15 mol) 4-[2-(4-pyridinyl)-ethenyl]-phenol, 21 g potassium carbonate, 750 ml butanone and 33 ml (0.23 mol) 4-bromobutyric acid ethyl ester to reflux for 24 h, filters, evaporates the filtrate, mixes with water, extracts with dichloromethane, dries the extract, evaporates the triturates the residue with ether. There remain 42.3 g of title compound (89% of theory) of the m.p. 83°–85° C.

EXAMPLE 5

In a manner analogous to that described in Example 4, one obtains:

| designation | yield % | melting point °C. (solvent) |
|---|---|---|
| a) 4-{4-[2-(4-pyridinyl)-ethyl]-phenoxy}-butyric acid ethyl ester from 4-[2-(4-pyridinyl)-ethyl]-phenol and 4-bromobutyric acid ethyl ester | 95 | oil |
| b) 5-{4-[2-(4-pyridinyl)-ethyl]-phenoxy}-valeric acid ethyl ester from 4-[2-(4-pyridinyl)-ethyl]-phenol and 5-bromovaleric acid ethyl ester | 90 | oil |
| c) 6-{4-[2-(4-pyridinyl)-ethyl]-phenoxy}-caproic acid ethyl ester from 4-[2-(4-pyridinyl)-ethyl]-phenol and 6-bromocaproic acid ethyl ester | 95 | oil |
| d) 4-[4-(3-pyridinylmethyl)-phenoxy]-butyric acid ethyl ester from 4-(3-pyridinylmethyl)-phenol and 4-bromobutyric acid ethyl ester | 90 | oil |
| e) 4-{3-[2-(4-pyridinyl)-ethenyl]-phenoxy}-butyric acid ethyl ester from 3-[2-(4-pyridinyl)-ethenyl]-phenol and 4-bromobutyric acid ethyl ester | 90 | oil |
| f) 4-{3-[2-(4-pyridinyl)-ethyl]-phenoxy}-butyric acid ethyl ester from 3-[2-(4-pyridinyl)-ethyl]-phenol and 4-bromobutyric acid ethyl ester | 95 | oil |
| g) 4-{3-[2-(2-pyridinyl)-ethenyl]-phenoxy}-butyric acid ethyl ester from 3[2-(2-pyridinyl)-ethenyl]-phenol and 4-bromobutyric acid ethyl ester | 95 | oil |
| h) 4-{3-[2-(2-pyridinyl)-ethyl]-phenoxy}-butyric acid ethyl ester from 3-[2-(2-pyridinyl)-ethyl]-phenol and 4-bromobutyric acid ethyl ester | 90 | oil |
| i) 2-{3-[2-(2-pyridinyl)-ethyl]-phenoxy}-acetic acid ethyl ester from 3-[2-(2-pyridinyl)-ethyl]-phenol and bromoacetic acid ethyl ester | 90 | oil |
| j) 4-{4-[2-(3-methyl-4-pyridinyl)-ethyl]-phenoxy}-butyric acid ethyl ester from 4-[2-(3-methyl-4-pyridinyl)-ethyl]-phenol and 4-bromobutyric acid ethyl ester | 86 | oil |
| k) 4-{4-[2-(5-n-butyl-2-pyridinyl)-ethyl]-phenoxy}-butyric acid ethyl ester from 4-[2-(5-n-butyl-2-pyridinyl)-ethyl]-phenol and 4-bromobutyric acid ethyl ester | 95 | oil |

EXAMPLE 6

5-{2-[2-(2-Pyridinyl)-ethenyl]-phenoxy}-valeric acid ethyl ester

To the solution of 2.3 g (0.1 mol) sodium in 250 ml ethanol one adds 19.7 g 2-[2-(2-pyridinyl)-ethenyl]-phenol, stirs for 10 min at room temp., adds thereto 17.4 ml (0.11 mol) 5-bromovaleric acid ethyl ester and heats to reflux for 16 h. One evaporates, mixes with water, extracts with dichloromethane, dries the extract and evaporates. There remain 32.4 g of title compound (100% of theory) as oil.

EXAMPLE 7

In a manner analogous to that described in Example 6, one obtains:

| designation | yield % | melting point °C. (solvent) |
| --- | --- | --- |
| a) 4-[4-(4-pyridinyl-methyl)-phenoxy]-butyric acid ethyl ester from 4-(4-pyridinylmethyl)-phenol and 4-bromobutyric acid ethyl ester | 84 | oil |
| b) 4-{4-[3-(4-pyridinyl)-propyl]-phenoxy}-butyric acid ethyl ester from 4-[3-(4-pyridinyl)-propyl]-phenol and 4-bromobutyric acid ethyl ester | 93 | oil |
| c) 5-{2-[2-(2-pyridinyl)-ethyl]-phenoxy}-valeric acid ethyl ester from 2-[2-(2-pyridinyl)-ethyl]-phenol and 5-bromovaleric acid ethyl ester | 71 | oil |
| d) 2-{4-[2-(4-pyridinyl)-ethyl]-phenoxy}-acetic acid ethyl ester from 4-[2-(4-pyridinyl)-ethyl]-phenol and bromoacetic acid ethyl ester | 52 | oil |
| e) 2-{4-[2-(2-pyridinyl)-ethyl]-phenoxy}-acetic acid ethyl ester from 4-[2-(2-pyridinyl)-ethyl]-phenol and bromoacetic acid ethyl ester | 67 | oil |

EXAMPLE 8

6-{4-[2-(4-Pyridinyl)-ethyl]-phenoxy}-caproic acid

A mixture of 11.3 g (33 mol) of compound of Example 5 c and 110 ml 1N caustic soda lye is heated to reflux for 2 h. One allows to cool, washes with ether, adjusts the aqueous phase to pH 5 and filters off the precipitate. One isolates 8.7 g of title compound (85% of theory) of the m.p. 180°–182° C.

EXAMPLE 9

In a manner analogous to that described in Example 8, one obtains:

| designation | yield (%) | melting point °C. (solvent) |
| --- | --- | --- |
| a) 4-{4-[2-(4-pyridinyl)-ethenyl]-phenoxy}-butyric acid from compd. of Example 4 | 55 | 271–273 (water) |
| b) 4-[2-(2-pyridinyl)-ethenyl]-benzoic acid from compd. of Example 3 | 90 | >300 (water) |
| c) 4-{4-[2-(4-pyridinyl)-ethyl]-phenoxy}-butyric acid from compd. of Example 5a | 81 | 216–218 (water) |
| d) 5-{4-[2-(4-pyridinyl)-ethyl]-phenoxy}-valeric acid from compd. of Example 5b | 80 | 110–112 (water) |
| e) 4-[4-(4-pyridinyl-methyl)-phenoxy]-butyric acid from compd. of Example 7a | 43 | 135–137 (water) |
| f) 4-{4-[3-(4-pyridinyl)-propyl]-phenoxy]-}butyric acid from compd. of Example 7b | 84 | 100–101 (water) |
| g) 4-[4-(3-pyridinyl-methyl)-phenoxy]-butyric acid from compd. of Example 5d | 55 | 118–122 (water) |
| h) 4-{3-[2-(4-pyridinyl)-ethenyl]-phenoxy}-butyric acid from compd. of Example 5e | 52 | 156–158 (water) |
| i) 4-{3-[2-(4-pyridinyl)-ethyl]-phenoxy}-butyric acid from. compd. of Example 5f | 47 | 114–116 (water) |
| j) 4-{3-[2-(2-pyridinyl)-ethenyl]-phenoxy}-butyric acid from compd. of Example 5g | 22 | 110–112 (ether) |
| k) 4-{3-[2-(2-pyridinyl)-ethyl]-phenoxy}-butyric acid from compd. of Example 5H | 36 | 78–80 (ethyl acetate) |
| l) 4-[2-(4-pyridinyl)-ethyl]-phenoxyacetic acid from compd. of Example 7d | 58 | 214–218 (water) |
| m) 3-[2-(2-pyridinyl)-ethyl]-phenoxyacetic acid from compd. of Example 5i | 15 | 88–90 (water) |
| n) 4-{4-[2-(3-methyl-4-pyridinyl)-ethyl]-phenoxy}-butyric acid from compd. of Example 5j | 21 | 168–170 (ethyl acetate) |
| o) 4-{4-[2-(4-pyridinyl)-ethenyl]-phenyl-methoxy}-benzoic acid from compd. of Example 23i | 95 | >300 (water) |
| p) 4-{4-[2-(5-n-butyl-2-pyridinyl)-ethyl]-phenoxy}-butyric acid from compd. of Example 5k | 28 | 108–110 (water) |

EXAMPLE 10

5-{2-[2-(2-Pyridinyl)-ethenyl]-phenoxy}-valeric acid

A mixture of 32.5 g (0.1 mol) of compound of Example 6, 450 ml 50 percent ethanol and 27 g potassium carbonate is heated under reflux for 2 h, evaporated, the residue taken up in water, washed with ether, the aqueous phase adjusted to pH 6.5 and the precipitate filtered off. After trituration with ether, one isolates 12.1 g of title compound (41% of theory) of the m.p. 90°–93° C.

EXAMPLE 11

In a manner analogous to that described in Example 10, one obtains:

| designation | yield % | melting point °C. (solvent) |
|---|---|---|
| a) 5-{2-[2-(2-pyridinyl)-ethyl]-phenoxy}-valeric acid from compd. of Example 7c | 75 | 66–68 (water) |
| b) 2-{4-[2-(2-pyridinyl)-ethyl]-phenoxy}-acetic acid from compd. of Example 7e | 91 | 135–137 (water) |

EXAMPLE 12

2-{4-{4-[2-(4-Pyridinyl)-ethenyl]-phenoxy}-butylthio}-benzoic acid

A mixture of 5.0 g (12 mmol) of compound of Example 2f, 100 ml ethanol and 100 ml 1N caustic soda lye is heated under reflux for 1 h, subsequently cooled, washed with ether, the aqueous phase adjusted to pH 6 and the precipitate filtered off. After trituration with ether, there remain 2.3 g of title compound (47% of theory) of the m.p. 229°–231° C.

EXAMPLE 13

In a manner analogous to that described in Example 12, one obtains: 2-{4-{4-[2-(4-pyridinyl)-ethyl]-phenoxy}-butylthio}-benzoic acid hydrochloride from compd. of Example 2 g; yield 85%, m.p. 102°–104° C. (from water).

EXAMPLE 14

2-{3-{4-[2-(4-Pyridinyl)-ethyl]-phenoxy}-propylthio}-benzoic acid

To the solution of 1.3 g (58 mmol) sodium in 100 ml ethanol one adds 5.7 g (29 mmol) 4-[2-(4-pyridinyl)-ethyl]-phenol, stirs for 10 min at room temperature, adds thereto 6.7 g (29 mmol) 2-(3-chloropropylthio)-benzoic acid and heats under reflux for 12 h. One allows to cool, filters, evaporates the filtrate, takes up in water, washes with ether, adjusts the aqueous phase to pH 5 and extracts with dichloromethane. After chromatography of the extract on silica gel and trituration with ligroin, one isolates 2.1 g of title compound (19% of theory) of the m.p. 151°–153° C.

EXAMPLE 15

5-{4-{4-[2-(4-Pyridinyl)-ethenyl]-phenoxy}butyl}-1H-tetrazole

A mixture of 5.3 g (19 mmol) of compound of Example 1, 3.7 g (57 mmol) sodium azide, 3.0 g (57 mmol) ammonium chloride and 40 ml N,N-dimethylformamide is stirred for 3 days at 125° C. One adds thereto a further 2.5 g sodium azide and 2.0 g ammonium chloride, stirs for a further 6 h at 125° C., evaporates, takes up the residue in water, extracts with dichloromethane, dries, evaporates and triturates with 2-propanol. There remain 2.7 g of title compound (44% of theory) of the m.p. 158°–159° C.

EXAMPLE 16

In a manner analogous to that described in Example 15, one obtains:

| designation | yield % | melting point °C. (solvent) |
|---|---|---|
| 1) 5-{4-{[2-(4-pyridinyl)-ethenyl]-phenoxymethyl}-phenyl}-1H tetrazole from compd. of Example 2a | 44 | 205–207 (water) |
| b) 5-{4-{4-[2-(2-pyridinyl)-ethenyl]-phenoxy}-butyl}-1H-tetrazole from compd. of Example 2b | 50 | 152–154 (water) |
| c) 5-{4-{2-[2-(4-pyridinyl)-ethenyl]-phenoxy}-butyl}-1H-tetrazole from compd. of Example 2c | 35 | 161–163 (ether) |
| d) 5-{4-{3-[2-4-pyridinyl)-ethenyl]-phenoxy}-butyl}-1H-tetrazole from compd. of Example 2d | 35 | 132–135 (ether) |
| e) 5-{4-{3-[2-(2-pyridinyl)-ethyl]-phenoxy}-butyl}-1H-tetrazole from compd. of Example 2e | 28 | oil |
| f) 5-(4-{4-[2-(4-pyridinyl)-ethenyl]-phenylmethoxy}-phenyl)-1H-tetrazole sodium from compd. of Example 2l | 61 | 264–266 (ethanol) |

EXAMPLE 17

4-{4-[2-(4-Pyridinyl)-ethenyl]-phenoxy}-butyric acid N-(1H-tetrazol-5-yl)-amide

To a solution of 5.6 g (20 mmol) of compound of Example 9a in 40 ml N,N-dimethylformamide one adds 3.6 g (22 mmol) N,N'-carbonyldiimidazole, stirs for 1 h at 100° C., adds thereto 1.8 g (22 mmol) 5-amino-1H-tetrazole, stirs for 3 h at 100° C., pours into water, filters off, suspends the precipitate in hot water and adjusts to pH 6. One filters and obtains 3.5 g of title compound (50% of theory) of the m.p. 274°–276° C.

EXAMPLE 18

In a manner analogous to that described in Example 17, one obtains:

| designation | yield % | melting point °C. (solvent) |
|---|---|---|
| a) 4-[2-(pyridinyl)-ethenyl]-benzoic acid N-(1H-tetrazol-5-yl)-amide sodium salt from compd. of Example 9b | 52 | >300 (water) |
| b) 4-{4-[2-4-pyridinyl)-ethyl]-phenoxy}-butyric acid N-(1H-tetrazol-5-yl)-amide from compd. of Example 9c | 38 | 231–232 (water) |
| c) 5-{2-[2-(2-pyridinyl)-ethenyl]-phenoxy}-valeric acid N-(1H-tetrazol-5-yl)-amide from compd. of Example 10 | 27 | 109–111 ether) |

-continued

| designation | yield % | melting point °C. (solvent) |
|---|---|---|
| d) 5-{4-[2-(4-pyridinyl)-ethyl]-phenoxy}-valeric acid N-(1H-tetrazol-5-yl)-amide from compd. of Example 9d | 50 | 170–173 (ether) |
| e) 6-{4-[2-(4-pyridinyl)-ethyl]-phenoxy}-caproic acid N-(1H-tetrazol-5-yl)-amide from compd. of Example 8 | 52 | 220–222 (ether) |
| f) 4-[4-(4-pyridinylmethyl)-phenoxy]-butyric acid N-1H-tetrazol-5-yl)-amide from compd. of Example 9e | 40 | 214–216 (water) |
| g) 4-{4-[3-(4-pyridinyl)-propyl]-phenoxy}-butyric acid N-(1H-tetrazol-5-yl)-amide sodium salt from compd. of Example 9f | 45 | 178–180 (water) |
| h) 5-{2-[2-(2-pyridinyl)-ethyl]-phenoxy}-valeric acid N-(1H-tetrazol-5-yl)-amide from compd. of Example 11a | 77 | 155–157 (ethyl acetate) |
| i) 4-[4-(3-pyridinyl-methyl)-phenoxy]-butyric acid N-(1H-tetrazol-5-yl)-amide sodium salt from compd. of Example 9g | 87 | 235–237 (ethanol) |
| j) 4-{3-[2-(4-pyridinyl)-ethenyl]-phenoxy}-butyric acid N-(1H-tetrazol-5-yl)-amide from compd. of Example 9h | 73 | 280–281 (ethanol) |
| k) 4-{3-[2-(4-pyridinyl)-ethyl]-phenoxy}-butyric acid N-(1H-tetrazol-5-yl)-amide from compd of Example 9i | 83 | 230–233 (ethanol) |
| l) 4-{3-[2-(2-pyridinyl)-ethenyl]-phenoxy}-butyric acid N-(1H-tetrazol-5-yl)-amide sodium salt from compd. of Example 9j | 77 | 199–204 (ethanol) |
| m) 4-{3-[2-(2-pyridinyl)-ethyl]-phenoxy}-butyric acid N-(1H-tetrazol-5-yl)-amide from compd. of Example 9k | 80 | 168–170 (ethanol) |
| n) 4-[2-(4-pyridinyl)-ethyl]-phenoxyacetic acid-N-(1H-tetrazol-5-yl)-amide dihydrate from compd. of Example 9l | 45 | 174–176 (water) |
| o) 3-[2-(2-pyridinyl)-ethyl]-phenoxyacetic acid N-(1H-tetrazol-5-yl)-amide sodium salt from compd. of Example 9m | 47 | 115–117 (water) |
| p) 4-{4-[2-(3-methyl-4-pyridinyl)-ethyl]-phenoxy}-butyric acid N-(1H-tetrazol-5-yl)-amide from compd. of Example 9n | 58 | 215–220 (water) |
| q) 4-{4-[2-(4-pyridinyl)-ethenyl]-phenyl-methoxy}-benzoic acid N-(1H-tetrazol-5-yl)-amide sodium salt from compd. of Example 9o | 91 | >300 (water) |
| r) 4-[2-(2-pyridinyl)-ethyl]-phenoxyacetic acid N-1H-tetrazol-5-yl)-amide from compd. of Example 11b | 37 | 178–180 (water) |
| s) 4-{4-[2-(5-n-butyl-2-pyridinyl)-ethyl]-phenoxy}-butyric acid N-(1H-tetrazol-5-yl)-amide sodium salt from compd. of Example 9p | 69 | 192–194 (water) |

EXAMPLE 19

N-Hydroxy-N-methyl-4-[2-(2-pyridinyl)-ethenyl]-benzamide

To a solution of 4.5 g (20 mmol) of compound of Example 9b in 150 ml dichloromethane and 2.8 ml triethylamine one adds dropwise at −10° C. a solution of 2.6 ml (20 mmol) chloroformic acid isobutyl ester and 20 ml dichloromethane, then stirs for 30 min, adds dropwise a solution of 1.7 g (36 mmol) N-methylhydroxylamine, 2.8 ml triethylamine and 60 ml dichloromethane, then stirs for 30 min, filters, washes the filtrate with sodium hydrogen carbonate solution, extracts with dil. caustic soda lye and adjusts the extract to pH 8. After extraction with dichloromethane, drying, evaporating and triturating with ether, one obtains 1.7 g of title compound (33% of theory) of the m.p. 135°–138° C.

EXAMPLE 20

In a manner analogous to that described in Example 19, one obtains:

| designation | yield % | melting point °C. (solvent) |
|---|---|---|
| a) N-hydroxy-N-methyl-4-{4-[2-(4-pyridinyl)-ethenyl]-phenoxy}-butyric acid amide from compd. of Example 9a | 24 | 140–142 (ether) |
| b) N-hydroxy-N-methyl-4-{4-[2-(4-pyridinyl)-ethyl]-phenoxy}-butyric acid amide from cmpd. of Example 9c | 28 | 90–93 (ether) |

EXAMPLE 21

4-{4-[2-(4-Pyridinyl)-ethenyl]-phenylmethoxy}-benzonitrile

A solution of 9.8 g (40 mmol) 4-(4-formylphenylmethoxy)-benzonitrile, 4 ml (40 mmol) 4-methylpyridine and 4 ml acetic acid anhydride is heated to 120° C. for 18 h. One mixes with water, extracts with dichloromethane, dries the extract, evaporates and triturates with ether. One isolates 6.1 g of title compound (49% of theory) of the m.p. 149°–150° C.

EXAMPLE 22

4-{4-[2-(4-Pyridinyl)-ethenyl]-phenylmethoxy}-benzonitrile

A mixture of 2.3 g (10 mmol) 4-[2-(4-chloromethylphenyl)-ethenyl]-pyridine, 1.2 g (10 mmol) 4-hydroxybenzonitrile, 1.4 g potassium carbonate and 10 ml butanone is heated under reflux for 18 h, filtered, the filtrate evaporated, taken up in ethyl acetate, washed with water, dried and evaporated. One obtains 2.0 g of title compound (64% of theory) of the m.p. 147°–149° C.

EXAMPLE 23

In a manner analogous to that described in Example 21, one obtains:

| designation | yield % | melting point °C. (solvent) |
|---|---|---|
| a) 4-{4-[2-(2-pyridinyl)-ethenyl]-phenylmethoxy}-benzonitrile from 4-(4-formylphenylmethoxy)-benzonitrile and 2-methylpyridine | 47 | 154–156 (ether) |
| b) 4-{2-[2-(2-pyridinyl)-ethenyl]-phenylmethoxy}-benzonitrile hydrochloride from 4-(2-formylphenylmethoxy)-benzonitrile and 2-methylpyridine | 32 | 178–180 (ethyl acetate) |
| c) 4-{2-[2-(4-pyridinyl)-ethenyl]-phenylmethoxy}-benzonitrile from 4-(2-formylphenylmethoxy)-benzonitrile and 4-methylpyridine | 27 | 85–87 (ethyl acetate) |
| d) 4-[2-(4-phenoxymethyl-phenyl)-ethenyl]-pyridine from 4-phenoxymethylbenzaldehyde and 4-methylpyridine | 31 | 150–152 (hexane) |
| e) 4-{2-[4-(4-chlorophenoxymethyl)-phenyl]-ethenyl}-pyridine from 4-(4-chlorophenoxymethyl)-benzaldehyde and 4-methylpyridine | 23 | 155–157 (hexane) |
| f) 4-{2-[4-(4-methoxyphenoxymethyl)-phenyl]-ethenyl}-pyridine from 4-(4-methoxyphenoxymethyl)-benzaldehyde and 4-methylpyridine | 34 | 154–156 (hexane) |
| g) 4-{2-[4-(4-methylphenoxymethyl)-phenyl]-ethenyl}-pyridine from 4-(4-methylphenoxymethyl)-benzaldehyde and 4-methylpyridine | 37 | 147–149 (hexane) |
| h) 4-{2-[4-(3,4-dichlorophenoxymethyl)-phenyl]-ethenyl}-pyridine from 4-(3,4-dichlorophenoxymethyl)-benzaldehyde and 4-methylpyridine | 29 | 116–118 (ethyl acetate) |
| i) 4-{4-[2-(4-pyridinyl)-ethenyl]-phenylmethoxy}-benzoic acid ethyl ester from 4-(4-formylphenylmethoxy)-benzoic acid ethyl ester and 4-methylpyridine | 42 | 146–148 (ethyl acetate) |

EXAMPLE 24

4-{4-[2-(4-Pyridinyl)-ethyl]-phenylmethoxy}-benzonitrile

A mixture of 2.0 g (6.4 mmol) of compound of Example 21, 30 ml ethanol, 60 ml tetrahydrofuran and 0.2 g 10 percent palladium-charcoal is hydrogenated at room temp. and 1 bar hydrogen pressure. After take up of the theoretical amount, it is filtered, evaporated and chromatographed on silica gel (elution agent isohexane/ethyl acetate), One obtains 1.3 g of title compound (65% of theory) of the m.p. 139°–140° C.

EXAMPLE 25

Inhibition of the antigen-caused constriction of passive sensitised guinea pig lung parenchyma strips in vitro (organ bath)

For the in vitro investigation of the compounds according to the invention, the inhibition of the antigen-caused constriction of passive sensitised guinea pig lung parenchyma strips was measured, as described in the following:

Pribright white guinea pigs were stunned by a neck blow and exsanguinated. The lungs were rinsed substantially free of blood in situ with Krebs buffer, pH 7.4.

Subsequently, the lungs were removed, cut up into strips (about 20×4×4 mm) and the strips passively sensitised for one hour at room temperature with a 1:50 dilution of a homologous anti-ovalbumin antiserum and then washed 1× with Krebs buffer.

The antiserum was previously produced according to DAVIES in guinea pigs of the same strain by repeated injection of ovalbumin (2×crystallised) with addition of complete Freund's adjuvant.

Until its use, the antiserum was stored at −18° C. undiluted.

Subsequently, the lung strips were suspended individually on an isometric measurement sensor with an initial tension of 1.2 g.

The baths were filled with Krebs buffer and continously gassed at 37° C. with $O_2$ (95%) and $CO_2$ (5%). The constrictions of the lung strips were recorded on a recorder via an amplifier.

After 30 minutes acclimatisation phase, histamine control spasms were produced for the recognition of the reaction ability of the organ pieces, washed, subsequently the test substance pre-incubated at 37° C. for 20 minutes and thereafter the ovalbumin-caused constriction initiated.

The inhibition actions of the compounds according to the invention were expressed as percentage reduction of the constriction amplitude of the "samples with test substance" in relationship to the "untreated control constrictions".

TABLE

Inhibition of the antigen-induced constriction on the passive sensitised lung parenchyma strips (guinea pigs).

| substance from Example | superfusion inhibition (%) concentration 10 μM |
|---|---|
| 12 | 42 |
| 18b | 32 |
| 18c | 33 |
| 14 | 56 |
| 15 | 56 |
| 18h | 53 |

We claim:

1. A compound of formula I

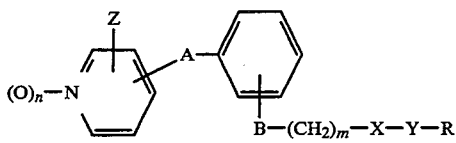

wherein B is a valency bond or —O—,
m is a whole number from 0 to 5,
n is 0 or 1,
X is a valency bond, —O—, or —S—,
Y is a valency bond,
Z is hydrogen, halogen, $C_1$–$C_6$-alkyl, or cyano,
R is —CN, COOH, COO($C_1$–$C_6$-alkyl), CONH-tetrazolyl, CON(OH)($C_1$–$C_6$-alkyl) or 5-(1H)-tetrazolyl, and
A can be —CH=CH—, or,
when R is —CN, CONH-tetrazolyl, CON(OH)($C_1$–$C_6$-alkyl) or 5-(1H)-tetrazolyl, A can also be $C_1$–$C_3$ alkylene, with the exception of the compound 4-[2-(4-)pyridinovinyl]carboxymethoxybenzene, and and the further exception of the compounds wherein Z=H, n=0, A=—CH=CH—, B=valency bond, m=0, X=valency bond, Y=valency bond, and R=—COO($C_1$–$C_6$-alkyl); and physiologically acceptable salts thereof.

2. A compound of formula I

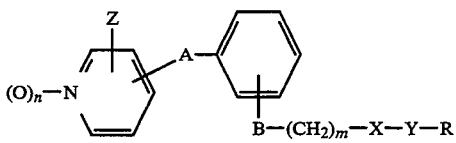

wherein A is a $C_1$–$C_3$ alkylene or —CH=CH—,
B is a valency bond or —O—,
m is a whole number from 0 to 5,
n is 0 or 1,
X is a valency bond, —O—, or —S—,
Y is a phenylene radical, which may be unsubsituted or substituted with $C_1$–$C_6$-alkyl, $C_1$–$C_6$-alkoxy, halogen, hydroxyl, or aminocarbonyl,
Z is hydrogen, halogen, $C_1$–$C_6$-alkyl, or cyano,
R is —CN, COOH, COO($C_1$–$C_6$-alkyl), CONH-tetrazolyl, CON(OH)($C_1$–$C_6$-alkyl) or 5-(1H)-tetrazolyl, and physiologically acceptable salts thereof.

3. A pharmaceutical composition comprising at least one compound of the formula I

wherein B is a valency bond or —O—,
m is a whole number from 0 to 5,
n is 0 or 1,
X is a valency bond, —O—, or —S—,
Y is a valency bond,
Z is hydrogen, halogen, $C_1$–$C_6$-alkyl, or cyano,
R is —CN, COOH, COO($C_1$–$C_6$-alkyl), CONH-tetrazolyl, CON(OH)($C_1$–$C_6$-alkyl) or 5-(1H)-tetrazolyl, and
A can be —CH=CH—, or,
when R is —CN, CONH-tetrazolyl, CON(OH)($C_1$–$C_6$-alkyl) or 5-(1H)-tetrazolyl, A can also be $C_1$–$C_3$ alkylene, and physiologically acceptable salts thereof, and carrier or adjuvant.

4. A pharmaceutical composition comprising at least one compound of the formula I

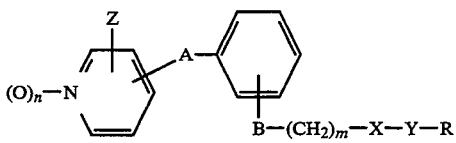

wherein A is a $C_1$–$C_3$ alkylene or —CH=CH—,
B is a valency bond or —O—,
m is a whole number from 0 to 5,
n is 0 or 1,
X is a valency bond, —O—, or —S—,
Y is a phenylene radical, which may be unsubstituted or substituted with $C_1$–$C_6$-alkyl, $C_1$–$C_6$-alkoxy, halogen, hydroxyl, or aminocarbonyl,
Z is hydrogen, halogen, $C_1$–$C_6$-alkyl, or cyano,
R is —CN, COOH, COO($C_1$–$C_6$-alkyl), CONH-tetrazolyl, CON(OH)($C_1$–$C_6$-alkyl) or 5-(1H)-tetrazolyl, and physiologically acceptable salts thereof, and carrier or adjuvant.

5. A method of treatment of allergic disease, inflammation-caused bronchospastic reactions, or inflammation-caused bronchoconstrictory reactions, said method comprising administering an effective amount of the pharmaceutical composition of claim 3.

6. A method of treatment of allergic disease, inflammation-caused bronchospastic reactions, or inflammation-caused bronchoconstrictory reactions, said method comprising administering an effective amount of the pharmaceutical composition of claim 4.

* * * * *